(12) United States Patent
Watanabe et al.

(10) Patent No.: US 10,809,262 B2
(45) Date of Patent: Oct. 20, 2020

(54) MULTIPLEX COLON CANCER MARKER PANEL

(71) Applicants: SHIMADZU CORPORATION, Kyoto-shi, Kyoto (JP); OSAKA UNIVERSITY, Suita-shi, Osaka (JP)

(72) Inventors: Makoto Watanabe, Kyoto (JP); Eiichi Matsuo, Kyoto (JP); Naoki Kaneko, Kyoto (JP); Toshiya Matsubara, Kyoto (JP); Osamu Nishimura, Suita (JP); Masaki Mori, Suita (JP); Hideo Matsuda, Suita (JP); Shigeto Seno, Suita (JP); Ichiro Takemasa, Suita (JP)

(73) Assignees: Shimadzu Corporation, Kyoto (JP); Osaka University, Osaka (JP)

( * ) Notice: Subject to any disclaimer, the term of this patent is extended or adjusted under 35 U.S.C. 154(b) by 0 days.

(21) Appl. No.: 14/852,308

(22) Filed: Sep. 11, 2015

(65) Prior Publication Data
US 2016/0003830 A1 Jan. 7, 2016

Related U.S. Application Data

(62) Division of application No. 13/723,133, filed on Dec. 20, 2012, now abandoned.

(30) Foreign Application Priority Data

Dec. 21, 2011 (JP) ................... 2011-280149

(51) Int. Cl.
*G01N 33/574* (2006.01)
*G01N 33/68* (2006.01)

(52) U.S. Cl.
CPC ... *G01N 33/57419* (2013.01); *G01N 33/6893* (2013.01)

(58) Field of Classification Search
CPC .............. G01N 33/57419; G01N 33/574
USPC ......................................... 506/13
See application file for complete search history.

(56) References Cited

U.S. PATENT DOCUMENTS

| | | | |
|---|---|---|---|
| 2006/0063156 A1 | 3/2006 | Willman et al. | |
| 2009/0191575 A1 | 7/2009 | Watanabe et al. | |
| 2013/0065258 A1 | 3/2013 | Watanabe et al. | |
| 2014/0148350 A1* | 5/2014 | Spetzler | G01N 33/574 506/9 |

FOREIGN PATENT DOCUMENTS

| | | |
|---|---|---|
| JP | 2002-323499 A | 11/2002 |
| JP | 2008-14937 A | 1/2008 |
| JP | 2011-517765 A | 6/2011 |
| WO | WO-2009/037572 A2 | 3/2009 |
| WO | WO-2011/063274 A2 | 5/2011 |
| WO | WO-2011/14668 A1 | 12/2011 |
| WO | WO 2012/024543 A1 * | 2/2012 |

OTHER PUBLICATIONS

Mackay et al (British Medical Journal, 1974, 4: 382-385).*
Watanabe, Makoto et al., "Clinical significance of circulating galectins as colorectal cancer markers", Oncology Reports, 2011, vol. 25, pp. 1217-1226.
Zhou, Jerry et al., "Surface antigen profiling of colorectal cancer using antibody microarrays with fluorescence multiplexing", Journal of Immunological Methods, 2010, vol. 355, pp. 40-51.

* cited by examiner

*Primary Examiner* — Sean E Aeder
(74) *Attorney, Agent, or Firm* — Morgan, Lewis & Bockius LLP

(57) ABSTRACT

The present invention provides a specific combination of colon cancer markers based on statistical knowledge, which is capable of detecting a larger number of colon cancer patients in an earlier stage while maintaining high specificity. A multiplex colon cancer marker panel comprising a combination of five colon cancer markers of Carcinoembryonic antigen-related cell adhesion molecule 5, Carbohydrate antigen 19-9, Galectin-4, APEX nuclease and Actin-related protein 2. A method for analyzing colon cancer markers using multiplex colon cancer marker panel.

18 Claims, 5 Drawing Sheets

MULTIPLEX COLON CANCER MARKER PANEL

CROSS REFERENCE TO RELATED APPLICATIONS

This application is a Divisional Application of patent application Ser. No. 13/723,133 filed on Dec. 20, 2012, which is based on Japanese Patent Application No. JP2011-280149 filed on Dec. 21, 2011, the entire contents of which are hereby incorporated by reference.

BACKGROUND OF THE INVENTION

Field of the Invention

The present invention relates to a technique for clinical diagnosis and screening of colon cancer. More specifically, the present invention relates to a multiplex colon cancer marker panel. Even more specifically, the present invention relates to a combination of colon cancer markers having a nigh ability to detect colon cancer.

Disclosure of the Related Art

As typical colon cancer markers, Carcinoembryonic antigen-related cell adhesion molecule 5 (CEA) and Carbohydrate Antigen 19-9 (CA19-9) are known. These colon cancer markers are actually used in clinical practice, but it has been demonstrated that they are not suitable for early diagnosis.

JP2008-14937 A (Patent Document 1) and Oncology Reports 2011, Vol. 25, pp 1217-26 (Non-Patent Document 1) report that novel Colon cancer-associated proteins have been identified by proteomic analysis of colon cancer tissues. Further, The Non-Patent Document 1 reports that Galectin-1, Galectin-3, and Galectin-4 are effective as plasma markers for colon cancer.

Patent Document 1: JP2008-14937 A
Non-Patent Document 1: Oncology Reports 2011, Vol. 25, pp 1217-26

SUMMARY OF THE INVENTION

Each of the colon cancer markers that have been previously reported cannot achieve a satisfactory detection rate of cancer patients (more specifically, sensitivity) when used as a single marker.

On the other hand, there is a case where markers are simply combined for the purpose of improving the reliability of diagnosis. It is true that the combined use of markers improves the detection rate of cancer patients, but specificity (i.e., the percentage of healthy individuals correctly diagnosed as healthy) is reduced. Therefore, it is necessary to minimize a reduction in specificity.

It is therefore an object of the present invention to provide a specific combination of colon cancer markers based on statistical knowledge, which is capable of detecting a larger number of colon cancer patients in an earlier stage while maintaining high specificity.

The present inventors have found that a specific combination of markers can achieve a hiqh detection rate of cancer patients while maintaining high specificity. Such findings have been found for the first time by the present invention.

The present invention includes the following inventions.
(1) A multiplex colon cancer marker panel comprising a combination of five colon cancer markers of Carcinoembryonic antigen-related cell adhesion molecule 5, Carbohydrate antigen 19-9, Galectin-4, APEX nuclease and Actin-related protein 2.
(2) A multiplex colon cancer marker panel comprising a combination of four colon cancer markers arbitrarily selected from five colon cancer markers of Carcinoembryonic antigen-related cell adhesion molecule 5, Carbohydrate antigen 19-9, Galectin-4, APEX nuclease and Actin-related protein 2.
(3) A multiplex colon cancer marker panel comprising a combination of three colon cancer markers of:
Carcinoembryonic antigen-related cell adhesion molecule 5, Carbohydrate antigen 19-9, and APEX nuclease;
Carcinoembryonic antigen-related cell adhesion molecule 5, Carbohydrate antigen 19-9, and Actin-related protein 2;
Carcinoembryonic antigen-related cell adhesion molecule 5, Galectin-4, and APEX nuclease;
Carbohydrate antigen 19-9, Galectin-4, and APEX nuclease;
Carbohydrate antigen 19-9, Galectin-4, and Actin-related protein 2; or
Carbohydrate antigen 19-9, APEX nuclease, and Actin-related protein 2.
(4) A multiplex colon cancer marker panel comprising a combination of two colon cancer markers of Carbohydrate antigen 19-9 and APEX nuclease.
(5) A method for analyzing colon cancer markers, the method comprising the steps of:
acquiring respective measured values of five colon cancer markers of Carcinoembryonic antigen-related cell adhesion molecule 5, Carbohydrate antigen 19-9, Galectin-4, APEX nuclease, and Actin-related protein 2 in a biological sample derived from an individual;
normalizing the respective measured values of the five colon cancer markers to derive respective probability scores of the five colon cancer markers and deriving an average of the probability scores; and
evaluating the average of the probability scores based on whether the average is higher or lower than a criterion value for the five colon cancer markers.
(6) A method for analyzing colon cancer markers, the method comprising the steps of:
acquiring respective measured values of four colon cancer markers arbitrarily selected from five colon cancer markers of Carcinoembryonic antigen-related cell adhesion molecule 5, Carbohydrate antigen 19-9, Galectin-4, APEX nuclease, and Actin-related protein 2 in a biological sample derived from an individual;
normalizing the respective measured values of the four colon cancer markers to derive respective probability scores of the four colon cancer markers and deriving an average of the probability scores; and
evaluating the average of the probability scores based on whether the average is higher or lower than a criterion value for the four colon cancer markers.
(7) A method for analyzing colon cancer markers, the method comprising the steps of:
acquiring respective measured values of three colon cancer markers of:
Carcinoembryonic antigen-related cell adhesion molecule 5, Carbohydrate antigen 19-9, and APEX nuclease;
Carcinoembryonic antigen-related cell adhesion molecule 5, Carbohydrate antigen 19-9, and Actin-related protein 2;
Carcinoembryonic antigen-related cell adhesion molecule 5, Galectin-4, and APEX nuclease;
Carbohydrate antigen 19-9, Galectin-4, and APEX nuclease;

Carbohydrate antigen 19-9, Galectin-4, and Actin-related protein 2; or

Carbohydrate antigen 19-9, APEX nuclease, and Actin-related protein 2 in a biological sample derived from an individual;

normalizing the respective measured values of the three colon cancer markers to derive respective probability scores of the three colon cancer markers and deriving an average of the probability scores; and evaluating the average of the probability scores based on whether the average is higher or lower than a criterion value for the three colon cancer markers.

(8) A method for analyzing colon cancer markers, the method comprising the steps of:

acquiring respective measured values of two colon cancer markers of Carbohydrate antigen 19-9 and APEX nuclease in a biological sample derived from an individual;

normalizing the respective measured values of the two colon cancer markers to derive respective probability scores of the two colon cancer markers and deriving an average of the probability scores; and evaluating the average of the probability scores based on whether the average is higher or lower than a criterion value for the two colon cancer markers.

According to the present invention, it is possible to provide a specific combination of colon cancer markers based on statistical knowledge, which is capable of detecting a larger number of colon cancer patients in an earlier stage while maintaining high specificity. More specifically, colon cancer patients can be detected at high sensitivity by determining the quantities of expressed specific two or more colon cancer markers in blood samples (plasma samples) from individual subjects. By detecting cancer patients at high sensitivity, it is possible to make an early diagnosis and to select an appropriate cancer treatment, which as a result contributes to an improvement in QOL of patients. Further, the colon cancer marker panel according to the present invention is expected to be applied to colon cancer diagnostic reagents and colon cancer diagnostic equipment.

DETAILED DESCRIPTION OF THE INVENTION

[1. Colon Cancer Marker Panel]

Figure 1:
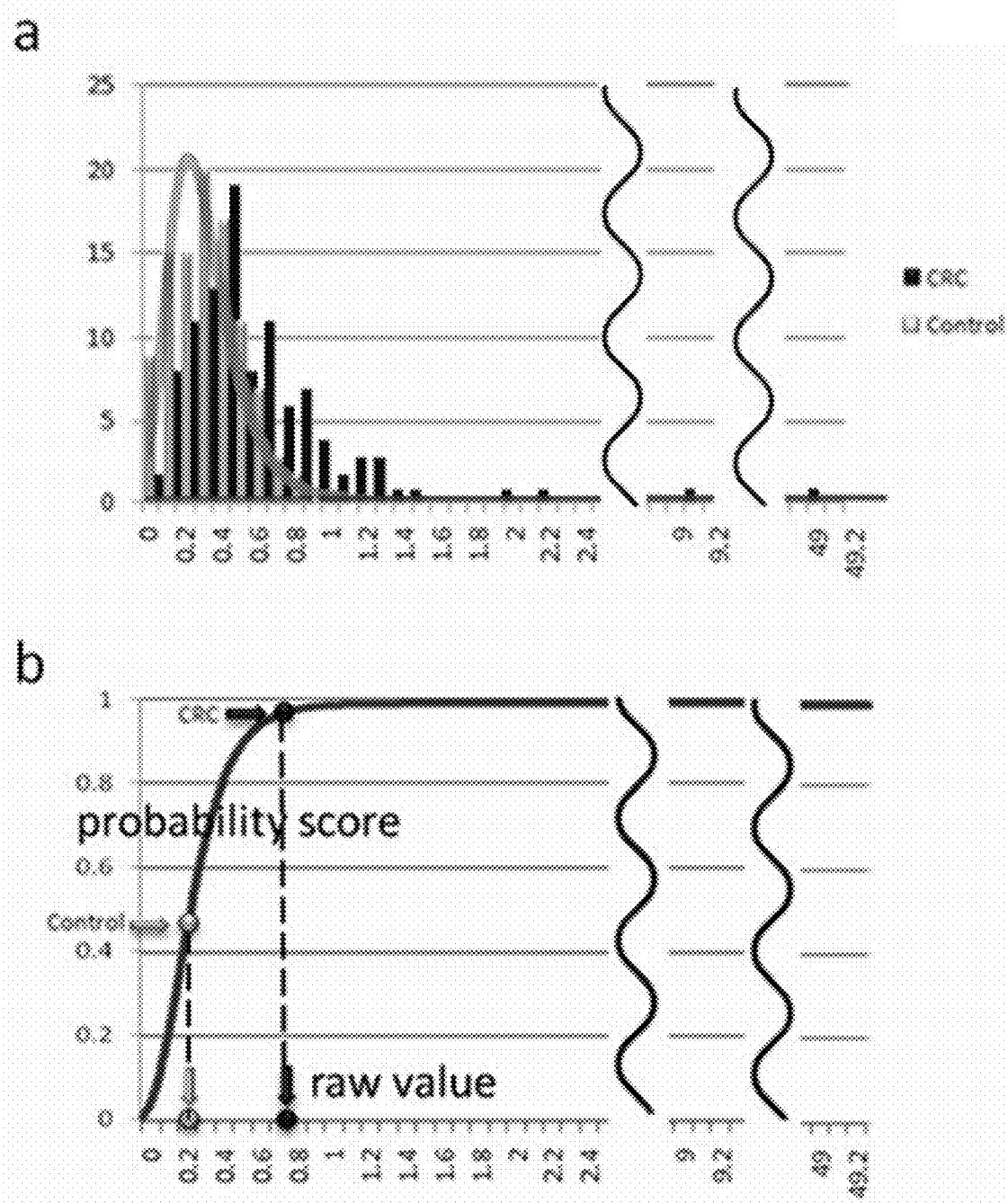
FIG. 1(a) shows a histogram representing the distribution of marker levels of Galectin-4 of healthy individuals (Control) and a histogram representing the distribution of marker levels of Galectin-4 of colon cancer patients (CRC), wherein the histogram of healthy individuals is given by gray bars and the histogram of colon cancer patients is given by black bars, and the horizontal axis represents the marker level and the vertical axis represents the number of samples.
FIG. 1(b) shows a curve of probability score obtained by converting the marker levels based on the cumulative distribution function of an extreme-value distribution shown in FIG. 1(a), wherein the horizontal axis represents the marker level (raw value) and the vertical axis represents the probability score.

The present invention provides a colon cancer marker panel comprising specific two or more colon cancer markers. The colon cancer marker panel according to the present invention is constituted from two to five colon cancer markers, and the expression of each of the markers is increased by colon cancer.

The colon cancer marker panel constituted from five colon cancer markers includes Carcinoembryonic antigen-related cell adhesion molecule 5 (hereinafter, referred to as "CEA"), Carbohydrate antigen 19-9 (hereinafter, referred to as "CA19-9"), Galectin-4, APEX nuclease (DNA-(apurinic or apyrimidinic site) lyase) (hereinafter, referred to as "APEX1"), and Actin-related protein 2 (hereinafter, referred to as "ACTR2").

The colon cancer marker panel constituted from four colon cancer markers includes four colon cancer markers arbitrarily selected from the above-mentioned five colon cancer markers. Specific combinations of the four colon cancer markers are CEA, CA19-9, Galectin-4, and APEX1; CEA, CA19-9, Galectin-4, and ACTR2; CEA, CA19-9, APEX1, and ACTR2; CEA, Galectin-4, APEX1, and ACTR2; and CA19-9, Galectin-4, APEX1, and ACTR2.

The colon cancer marker panel constituted from three colon cancer markers includes specific three colon cancer markers selected from the above-mentioned five colon cancer markers. Specific combinations of the three colon cancer markers are CEA, CA19-9, and Galectin-4; CEA, CA19-9, and APEX1; CEA, CA19-9, and ACTR2; CEA, Galectin-4 and APEX1; CA19-9, Galectin-4, and APEX1; CA19-9, Galectin-4, and ACTR2; and CA19-9, APEX1, and ACTR2.

The colon cancer marker panel constituted from two colon cancer markers includes specific two colon cancer markers selected from the above-mentioned five colon cancer markers. Specific combinations of the two colon cancer markers are CA19-9 and Galectin-4; and CA19-9 and APEX1.

[2. Method for Analyzing Colon Cancer Markers]

[2-1. Sample to be Analyzed]

An object to be analyzed by a method according to the present invention is a biological sample derived from an individual (human individual). The biological sample to be analyzed is preferably a blood sample. However, this is not intended to exclude a body fluid sample or a tissue sample other than a blood sample.

Examples of the blood sample include whole blood, blood plasma, and blood serum, and the like. The blood sample can be prepared by appropriately treating whole blood collected from an individual. When collected whole blood is treated to prepare a blood sample, treatment performed on the whole blood is not particularly limited as long as it is clinically acceptable. For example, anticoagulation treatment and centrifugal separation may be performed. The blood sample directly subjected to measurement of marker levels may be one that has been appropriately stored at low temperatures, for example, in a frozen state, in the course of or after its preparation. It is to be noted that the blood sample used in the present invention is discarded without being returned to an individual as its source.

[2-2. Colon Cancer Markers to be Measured]

The method according to the present invention absolutely includes the step of measuring each of colon cancer markers constituting the above-described colon cancer marker panel.

A high detection rate can be expected by performing the step of measuring two or more other colon cancer markers in addition to the step of measuring each of colon cancer markers constituting the above-described colon cancer marker panel. On the other hand, even when a high detection rate is achieved by increasing the number of markers used in combination, it is clinically meaningless if specificity is low. Therefore, the optimum number of markers can be determined using, as an index, a median AUC (Area Under the Curve) obtained by repeating analysis 100 times (which will be described later) per number of markers.

[2-3. Analysis of Colon Cancer Marker Levels]

The analysis of cancer marker levels according to the present invention is performed by acquiring respective measured values of colon cancer markers constituting the colon cancer marker panel, and using the measured values which are sigmoidally normalized based on an extreme-value distribution.

The parameters of the extreme-value distribution are determined using only the marker levels of samples of healthy individuals. The measured value of each of the markers is converted to a "probability score" by the cumulative distribution function of the extreme-value distribution. The probability score (hereinafter, sometimes simply referred to as a "score") refers to the probability that a patient has colon cancer at a certain marker level, and is a normalized value between 0 and 1.

An average value is derived from the respective scores derived from the respective measured marker values. Based on the score average determined in such a manner as described above, a diagnosis of colon cancer is made. When the score average of a sample is larger than a criterion value, the sample is regarded as positive, and when the score average of a sample is smaller than the criterion value, the sample is regarded as negative. When a sample is regarded as positive based on its score average, a human individual as a source of the sample can be diagnosed as having colon cancer.

A specific example of the criterion value to be compared with the score average value is a threshold value of average of colon cancer marker scores. The threshold value used in the present invention can be previously set depending on race, age, etc. The threshold value can be set by reference to averages of scores of the colon cancer markers converted by the above-described normalization of the measured quantity values of the respective colon cancer markers present in samples derived from individuals belonging to a healthy individual group and from individuals belonging to a colon cancer patient group.

As the threshold value, a cutoff value yielding high diagnostic accuracy is selected. The threshold value can be appropriately selected by those skilled in the art from cutoff values preferably yielding a specificity of 80% or higher, e.g., 95%. The upper limit of the specificity is not particularly limited, but may be, for example, 98%.

A method for setting the threshold value is appropriately selected by those skilled in the art. One example of the method is ROC Curve (Receiver Operating Characteristic Curve) analysis.

[2-4. Measurement Method]

In the method according to the present invention, the colon cancer markers are preferably measured by an assay based on biospecific affinity. The assay based on biospecific affinity is well-known to those skilled in the art and is not particularly limited. However, an immunoassay is preferred. Specific examples of the immunoassay include competitive and non-competitive immunoassays such as western blotting, radioimmunoassay, Enzyme-Linked ImmunoSorbent Assay (ELISA; including all sandwich, competitive, and direct immunoassays), immunoprecipitation, precipitation reaction, immunodiffusion, immunoagglutination, complement-binding reaction, immunoradiometric assay, fluoroimmunoassay, and protein A immunoassay. In the immunoassay, antibodies that bind to the colon cancer markers in a blood sample are detected. At this time, a colon cancer detection chip may be used, in which antibodies that bind to all the proteins constituting the colon cancer marker panel are immobilized onto the surface of one substrate.

The colon cancer markers are measured by bringing a sample into contact with antibodies under conditions where colon cancer marker proteins to be measured can form immunocomplexes with antibodies against the colon cancer marker proteins.

A specific protocol of the immunoassay can be easily selected by those skilled in the art.

Alternatively, the colon cancer markers may be measured based on mass spectrometry. A method of mass spectrometry is not particularly limited as long as it can perform quantitative analysis, and can be appropriately selected by those skilled in the art.

EXAMPLES

Hereinbelow, the present invention will be described more specifically with reference to the following examples, but is not limited to the examples.

Reference Example 1

In the following Reference Example 2 and Example 1, plasma samples were prepared in the following manner. About 15 mL of blood was collected from each individual into a BD Vacutainer CPT™ tube. After the collection of blood, the collected blood was immediately centrifuged (1,700×g, 4° C., 20 min) to obtain a supernatant as a plasma component (about 5 mL). The obtained plasma sample was stored at −80° C.

The plasma sample was thawed before measurement and diluted 5,000 to 20,000-fold to obtain a blood sample used to measure the concentrations of the colon cancer markers according to the present invention.

Reference Example 2

Out of the proteins identified by proteomic analysis using cancer tissues in JP2008-14937A, 40 proteins whose ELISA measurement systems have been established were selected as candidates for colon cancer markers. These 40 proteins are shown in Tables 1 to 8. In Tables 1 to 8, the protein names and gene names of the 40 proteins, existing ELISA kits, standard proteins, capture antibodies, detection antibodies, conjugated enzymes, secondary antibodies, and substrates are shown. It is to be noted that the protein names and the gene names in Tables are names registered in the UniProt database, "CA19-9" in Table 1 refers to carbohydrate antigen 19-9, recombinant proteins marked with 3) in Tables 2 and 3 were synthesized using "Transdirect insect cell" (manufactured by Shimadzu Corporation), and antibodies marked with 4) in Tables 2, 3 and 4 were prepared by immunizing synthetic peptides.

TABLE 1

| No. | Protein Name | Gene Name | ELISA Kit | Standard protein | Capture antibody |
|---|---|---|---|---|---|
| 1 | Carcinoembryonic antigen-related cell adhesion molecule 5 | CEACAM5 | Access CEA (Wako Pure Chemical Industries, Osaka, Japan) | | |
| 2 | | CA19-9 | SphereLight CA19-9 (Olympus, Tokyo, Japan) | | |
| 3 | Galectin-1 | LGALS1 | | Recombinant LGALS1 (Abnova, Taiwan) | Goat anti-human Galectin-1 pAb (R&D Systems, Minneapolis, MN) 5 µg/ml |
| 4 | Galectin-2 | LGALS2 | | Recombinant LGALS2 (R&D Systems,) | Goat anti-human Galectin-2 pAb (R&D) |
| 5 | Galectin-3 | LGALS3 | | Recombinant LGALS3 (R&D Systems) | Goat anti-human Galectin-3 pAb (R&D) 5 µg/ml |

| No. | Detection antibody | Conjugated enzyme | Secondary antibody | Substrate |
|---|---|---|---|---|
| 1 | | | | |
| 2 | | | | |
| 3 | Mouse anti-human Galectin-1 mAb (Abnova, Taiwan) 0.5 mg/ml | ALP | | Colorimetric ALP substrate |
| 4 | Goat anti-human Galectin-2 pAb (R&D) | HRP | | Chemiluminescent ALP substrate |
| 5 | Mouse anti-human Galectin-3 mAb (Abnova) 0.1 mg/ml | HRP | | HRP chromogene |

TABLE 2

| No. | Protein Name | Gene Name | ELISA Kit | Standard protein | Capture antibody |
|---|---|---|---|---|---|
| 6 | Galectin-4 | LGALS4 | | Recombinant LGALS4 (R&D Systems) | Goat anti-human Galectin-4 pAb (R&D) |
| 7 | Galectin-7 | LGALS7 | | Recombinant LGALS7 (R&D Systems) | Goat anti-human Galectin-7 pAb (R&D) |
| 8 | Vitronectin | VTN | Vitronectin EIA Kit (TAKARA BIO, Shiga, Japan) | | |
| 9 | Alpha-1-acid glycoprotein 2 | ORM2 | | Recombinant ORM2[3] | Rabbit anti-human ORM2 pAb[4] 5 mg/ml |
| 10 | Zyxin | ZYX | | Recombinant ZYX (Abnova) | Mouse anti-human Zyxin mAb (Invitrogen) 5 mg/ml |

TABLE 2-continued

| No. | Detection antibody | Conjugated enzyme | Secondary antibody | Substrate |
|---|---|---|---|---|
| 6 | Goat anti-human Galectin-4 pAb (R&D) | HRP | | HRP chromogene |
| 7 | Goat anti-human Galectin-7 pAb (R&D) | HRP | | Chemilumine scent ALP substrate |
| 8 | | | | |
| 9 | Rabbit anti-human Alpha 1 acid glycoprotein pAb (Abcam) 0.5 mg/ml | HRP | | HRP chromogene |
| 10 | Rabbit anti-human ZYX pAb (Proteintech Group, Chicago, IL) | | Anti-Rabbit IgG HRP (Invitrogen, Carlsbad, CA) 1/50000 | HRP chromogene |

TABLE 3

| No. | Protein Name | Gene Name | ELISA Kit | Standard protein | Capture antibody |
|---|---|---|---|---|---|
| 11 | Splicing factor 3B subunit 3 | SF3B3 | | Recombinant SF3B3[3)] | Goat anti-human SAP130 pAb (Abcam, Cambridge, UK) 5 mg/ml |
| 12 | Glycyl-tRNA synthetase | GARS | | Recombinant GARS[3)] | Rabbit anti-human GARS pAb[4)] 5 mg/ml |
| 13 | Alpha enolase | ENO1 | | Recombinant ENO1 (Abnova) | Mouse anti-human ENO1 mAb (Abnova) 2.5 mg/ml |
| 14 | Reticulocalbin-1 | RCN1 | | Recombinant RCN1 (Abnova) | Rabbit anti-human RCN1 pAb (Bethyl Laboratories) 2.5 µg/ml |
| 15 | Keratin, type I cytoskeletal 18 | KRT18 | M30 Apoptosense ® ELISA (PEVIVA, Stockholm, Sweden) | | |

| No. | Detection antibody | Conjugated enzyme | Secondary antibody | Substrate |
|---|---|---|---|---|
| 11 | Rabbit anti-human SF3B3 pAb[4)] 0.7 mg/ml | | Anti-Rabbit IgG HRP (Invitrogen) 1/50000 | HRP chromogene |
| 12 | Rabbit anti-human GARS pAb[4)] 0.4 mg/ml | ALP | | Colorimetric ALP substrate |
| 13 | Rabbit anti-human ENO1 pAb (Proteintech Group) 0.3 mg/ml | | Anti-Rabbit IgG HRP (Invitrogen) 1/50000 | HRP chromogene |
| 14 | Mouse anti-human RCN1 mAb (Abnova) 0.5 mg/ml | | Anti-Mouse IgG HRP (Invitrogen) 1/10000 | HRP chromogene |
| 15 | | | | |

TABLE 4

| No. | Protein Name | Gene Name | ELISA Kit | Standard protein | Capture antibody |
|---|---|---|---|---|---|
| 16 | Protein S100-A8/8100-S9 | S100A8/A9 | Calprotectin, Human, ELISA kit (Hycult biotechnology, Plymouth Meeting, PA) | | |

TABLE 4-continued

| No. | Protein Name | Gene Name | ELISA Kit | Standard protein | Capture antibody |
|---|---|---|---|---|---|
| 17 | Heat shock protein beta-1 | HSPB1 | Hsp27 ELISA Kit (Calbiochem, Darmstadt, Germany) | | |
| 18 | Receptor-type tyrosine-protein phosphatase alpha | PTPRA | | Recombinant PTPRA (SignalChem, British Columbia, Canada) | Rabbit anti-human PTPRA pAb (Proteintech Group) 3 mg/ml |
| 19 | Endoplasmin | HSP90B1 | | Recombinant TRA1 (Abnova) | Mouse anti-human TRA1 mAb (Proteintech Group) 5 mg/ml |
| 20 | Complement factor H | CFH | | Native Factor H (AbD serotec, Kidlington, UK) | Sheep anti-human Factor H pAb (Gene Tex, Irvine, CA) 5 µg/ml |

| No. | Detection antibody | Conjugated enzyme | Secondary antibody | Substrate |
|---|---|---|---|---|
| 16 | | | | |
| 17 | | | | |
| 18 | Rabbit anti-human PTPRA pAb[4)] 1 mg/ml | ALP | | Chemilumine scent ALP substrate |
| 19 | Rabbit anti-human TRA1 pAb (Proteintech Group) 0.5 mg/ml | | Anti-Rabbit IgG ALP (Invitrogen) 1/20000 | Chemilumine scent ALP substrate |
| 20 | Sheep anti-human Factor H pAb (Gene Tex) 0.5 µg/ml | ALP | | Colorimetric ALP substrate |

TABLE 5

| No. | Protein Name | Gene Name | ELISA Kit | Standard protein | Capture antibody |
|---|---|---|---|---|---|
| 21 | Vimentin | VIM | | Recombinant Vimentin (assay designs, Ann Arbor, MI) | Mouse anti-human Vimentin mAb (Abcam) 3 mg/ml |
| 22 | DNA-(apurinic or apyrimidinic site) lyase | APEX1 | | Recombinant Apurinic/Apyrimidinic Endonuclease (ALEXIS BIOCHEMICALS, San Diego, CA) | Mouse anti-human APE1 mAb (Abcam) 3 mg/ml |
| 23 | Serine/arginine-rich splicing factor 3 | SFRS3 | | Recombinant SFRS3 (Abnova) | Rabbit anti-human SFRS3 pAb (Abcam) 1 mg/ml |
| 24 | F-box only protein 40 | FBXO40 | | Recombinant FBXO40 (Abnova) | Rabbit anti-human FBXO40 pAb (Atlas Antibodies, Stockholm, Sweden) 2 µg/ml |
| 25 | Fermitin family homolog 2 | FERMT2 | | Recombinant PLEKHC1 (Abnova) | Rabbit anti-human FERMT2 pAb (Proteintech Group) 5 mg/ml |

| No. | Detection antibody | Conjugated enzyme | Secondary antibody | Substrate |
|---|---|---|---|---|
| 21 | Rabbit anti-human Vimentin pAb (Abcam) 1 mg/ml | | Anti-Rabbit IgG HRP (Invitrogen) 1/50000 | HRP chromogene |
| 22 | Mouse anti-human APE1 mAb (Abcam) 0.2 mg/ml | HRP | | HRP chromogene |
| 23 | Mouse anti-human SFRS3 mAb (Abnova) 1 mg/ml | | Anti-Mouse IgG HRP (Invitrogen) 1/10000 | HRP chromogene |

TABLE 5-continued

| | | | | |
|---|---|---|---|---|
| 24 | Mouse anti-human FBXO40 mAb (Abnova) 0.5 mg/ml | | Anti-Mouse IgG HRP (Invitrogen) 1/10000 | HRP chromogene |
| 25 | Goat anti-human Mig-2 pAb (Santa cruz biotechnology, Santa cruz, CA) 2.5 mg/ml | | Anti-Goat IgG HRP (Invitrogen) 1/50000 | HRP chromogene |

TABLE 6

| No. | Protein Name | Gene Name | ELISA Kit | Standard protein | Capture antibody |
|---|---|---|---|---|---|
| 26 | Ras-related protein Rab-18 | RAB18 | | Recombinant RAB18 (Abnova) | Mouse anti-human RAB18 mAb (Proteintech Group) 5 mg/ml |
| 27 | Thiosulfate sulfurtransferase | TST | | Recombinant TST (Abnova) | Rabbit anti-human TST pAb (Proteintech Group) 2 mg/ml |
| 28 | Inorganic pyrophosphatase | PPA1 | | Recombinant PP (Abnova) | Rabbit anti-human PPA1 pAb (Atlas Antibodies) 5 µg/ml |
| 29 | 6-phosphogluconolactonase | PGLS | | Recombinant PGLS (Abnova) | Rabbit anti-human PGLS pAb (Abcam) 5 mg/ml |
| 30 | 26S proteasome non-ATPase regulatory subunit 3 | PSMD3 | | Recombinant PSMD3 (Abnova) | Rabbit anti-human PSMD3 pAb (Proteintech Group) 3 mg/ml |

| No. | Detection antibody | Conjugated enzyme | Secondary antibody | Substrate |
|---|---|---|---|---|
| 26 | Rabbit anti-human RAB18 pAb (Proteintech Group) 1 mg/ml | | Anti-Rabbit IgG HRP (Invitrogen) 1/50000 | HRP chromogene |
| 27 | Rabbit anti-human TST pAb (Abcam) 1 mg/ml | HRP | | HRP chromogene |
| 28 | Mouse anti-human PPA1 mAb (Abnova) 0.5 mg/ml | | Anti-Mouse IgG HRP (Invitrogen) 1/10000 | HRP chromogene |
| 29 | Mouse anti-human PGLS mAb (Abnova) 0.5 mg/ml | | Anti-Mouse IgG HRP (Invitrogen) 1/10000 | HRP chromogene |
| 30 | Rabbit anti-human Proteasome 19S S3 pAb (NOVUS Biologicals, Littleton, CO) 0.5 mg/ml | HRP | | HRP chromogene |

TABLE 7

| No. | Protein Name | Gene Name | ELISA Kit | Standard protein | Capture antibody |
|---|---|---|---|---|---|
| 31 | Ubiquitin carboxyl-terminal hydrolase 13 | USP13 | | Recombinant USP13 (Abnova) | Rabbit anti-human USP13 pAb (Proteintech Group) 1 mg/ml |
| 32 | Signal recognition particle 9 kDa protein | SRP9 | | Recombinant SRP9 (ORIGENE, Rockville, MD) | Rabbit anti-human SRP9 pAb (Proteintech Group) 2 mg/ml |

TABLE 7-continued

| | | | | |
|---|---|---|---|---|
| 33 | GTP:AMP phosphotransferase mitochondrial | AK3 | Recombinant AK3 (Abnova) | Rabbit anti-human AK3 pAb (Proteintech Group) 1 mg/ml |
| 34 | 26S proteasome non-ATPase regulatory subunit 13 | PSMD13 | Recombinant PSMD13 (Abnova) | Rabbit anti-human PSMD13 pAb (Proteintech Group) 2 mg/ml |
| 35 | Cytochrome c1, heme protein, mitochondrial | CYC1 | Recombinant CYC1 (Abnova) | Rabbit anti-human CYC1 pAb (Proteintech Group) 2 mg/ml |

| No. | Detection antibody | Conjugated enzyme | Secondary antibody | Substrate |
|---|---|---|---|---|
| 31 | Rabbit anti-human USP13 pAb (Abcam) 0.5 mg/ml | HRP | | HRP chromogene |
| 32 | Goat anti-human SRP9 pAb (Santa cruz) 0.5 mg/ml | | Anti-Goat IgG HRP (Invitrogen) 1/50000 | HRP chromogene |
| 33 | Rabbit anti-human AK3 pAb (Abcam) 1 mg/ml | HRP | | HRP chromogene |
| 34 | Rabbit anti-human PSMD13 pAb (Abcam) 1 mg/ml | HRP | | HRP chromogene |
| 35 | Rabbit anti-human CYC1 pAb (GeneTex) 0.4 µg/ml | HRP | | HRP chromogene |

TABLE 8

| No. | Protein Name | Gene Name | ELISA Kit | Standard protein | Capture antibody |
|---|---|---|---|---|---|
| 36 | Protein disulfide-isomerase A4 | PDIA4 | | Recombinant PDIA4 (Abnova) | Rabbit anti-human PDIA4 pAb (Atlas Antibodies) 1 µg/ml |
| 37 | Proteasome subunit alpha type-7 | PSMA7 | | Recombinant PSMA7 (Abnova) | Rabbit anti-human PSMA7 pAb (Proteintech Group) 2 mg/ml |
| 38 | Voltage-dependent anion-selective channel protein 1 | VDAC1 | | Recombinant VDAC1 (Abnova) | Rabbit anti-human VDAC1 pAb (Proteintech Group) 3 mg/ml |
| 39 | Actin-related protein 2 | ACTR2 | | Recombinant ACTR2 (Abnova) | Rabbit anti-human ACTR2 pAb (Proteintech Group) 2 mg/ml |
| 40 | Paraneoplastic antigen Ma2 | PNMA2 | | Recombinant PMNA2 (ORIGENE) | Rabbit anti-human PNMA2 pAb (Atlas Antibodies) 1 µg/ml |

| No. | Detection antibody | Conjugated enzyme | Secondary antibody | Substrate |
|---|---|---|---|---|
| 36 | Rabbit anti-human ERp72 pAb (Abcam) 1 mg/ml | HRP | | HRP chromogene |
| 37 | Mouse anti-human PSMA7 mAb (Abnova) 0.5 mg/ml | | Anti-Mouse IgG HRP (Invitrogen) 1/10000 | HRP chromogene |
| 38 | Rabbit anti-human VDAC1 pAb (Abcam) 1 mg/ml | HRP | | HRP chromogene |

TABLE 8-continued

| | | | | |
|---|---|---|---|---|
| 39 | Mouse anti-human ACTR2 mAb (Abnova) 0.5 mg/ml | HRP | | HRP chromogene |
| 40 | Mouse anti-human PNMA2 mAb (Abnova) 0.2 mg/ml | HRP | | HRP chromogene |

Plasma samples of patients whose informed consent had been obtained in accordance with the ethical guidelines of Faculty of Medicine of Osaka University were analyzed in the following manner. In the following analysis, "sensitivity" refers to the percentage of colon cancer patients who are correctly diagnosed as having colon cancer, and "specificity" refers to the percentage of healthy individuals as healthy who are correctly diagnosed, and "false-positive rate" refers to the percentage of healthy individuals who are diagnosed as having colon cancer.

The plasma samples were prepared according to the method described in Reference Example 1 from blood collected from 105 colon cancer patients and 100 healthy individuals. The concentrations of the 40 proteins in each of the plasma samples of the colon cancer patients and the healthy individuals were measured using the ELISA measurement systems shown in Tables 1 to 8.

cancer determined using the cutoff value of each of the markers in healthy individuals vs colon cancer patients (namely, Control vs CRC) are shown. It is to be noted that the cutoff values and the sensitivities are values when the specificity is 95% (i.e., when an allowable false-positive rate is 5%). Further, the significant difference in concentration was based on verification using Mann-Whitney test. The stages of colon cancer are based on TMN classification, and primary cancer is represented as Stage 0 (in-situ cancer), Stage I, and Stage II, and lymph node metastatic cancer is represented as Stage III and Stage IV (the same shall apply hereinafter).

As shown in Table 9, when these 13 proteins were used alone as markers, sensitivity for all stages was about 40% at a maximum. That is, it can be said that these proteins are poor in sensitivity when used as single markers.

TABLE 9

| Protein Name | Gene Name | Control vs CRC AUC | Control vs CRC P value | Cutoff Value Concentration | Cutoff Value Probability Score | Sensitivity Stage 0 (N = 6) | Sensitivity Stage I (N = 28) | Sensitivity Stage II (N = 25) | Sensitivity Stage III (N = 27) | Sensitivity Stage IV (N = 19) | Sensitivity All Stages (N = 105) |
|---|---|---|---|---|---|---|---|---|---|---|---|
| Carcinoembryonic antigen-related cell adhesion molecule 5 | CEACAM5 | 0.744 | <0.001 | 5 (ng/mL) | 0.957 | 0.167 | 0.071 | 0.360 | 0.370 | 0.684 | 0.333 |
| | (CA19-9) | 0.834 | <0.001 | 37 (U/mL) | 0.995 | 0.000 | 0.036 | 0.160 | 0.111 | 0.526 | 0.171 |
| Galectin-4 | LGALS4 | 0.786 | <0.001 | 0.6075 (ng/mL) | 0.930 | 0.167 | 0.250 | 0.400 | 0.481 | 0.632 | 0.410 |
| DNA-(apurinic or apyrimidinic site) lyase | APEX1 | 0.731 | <0.001 | 1026 (ng/mL) | 0.967 | 0.167 | 0.036 | 0.240 | 0.185 | 0.211 | 0.162 |
| Actin-related protein 2 | ACTR2 | 0.696 | <0.0001 | 709.3 (ng/mL) | 0.910 | 0.167 | 0.036 | 0.160 | 0.148 | 0.105 | 0.114 |
| Vitronectin | VTN | 0.657 | <0.001 | 10.89 (mg/mL) | 0.992 | 0.167 | 0.286 | 0.280 | 0.370 | 0.211 | 0.286 |
| Galectin-1 | LGALS1 | 0.654 | 0.0001 | 364.2 (ng/mL) | 0.937 | 0.500 | 0.214 | 0.480 | 0.296 | 0.263 | 0.324 |
| Galectin-3 | LGALS3 | 0.647 | 0.0003 | 10.93 (ng/mL) | 0.933 | 0.000 | 0.179 | 0.320 | 0.296 | 0.263 | 0.248 |
| Keratin, type I cytoskeletal 18 | KRT18 | 0.638 | 0.0007 | 160.8 (U/L) | 0.964 | 0.167 | 0.107 | 0.200 | 0.074 | 0.368 | 0.171 |
| Proteasome subunit alpha type-7 | PSMA7 | 0.599 | 0.0128 | 520.8 (ng/mL) | 0.986 | 0.167 | 0.143 | 0.120 | 0.037 | 0.105 | 0.105 |
| Inorganic pyrophosphatase | PPA1 | 0.590 | 0.0253 | 536.1 (ng/mL) | 0.979 | 0.167 | 0.000 | 0.040 | 0.111 | 0.105 | 0.067 |
| Reticulocalbin-1 | RCN1 | 0.581 | 0.0195 | 36.77 (ng/mL) | 0.902 | 0.167 | 0.000 | 0.040 | 0.074 | 0.105 | 0.057 |
| Fermitin family homolog 2 | FERMT2 | 0.581 | 0.0446 | 600.0 (ng/mL) | 0.661 | 0.167 | 0.000 | 0.160 | 0.111 | 0.053 | 0.086 |

Out of the 40 markers, 13 proteins showed statistically-significant differences (p<0.05) between the colon cancer patients and the healthy individuals. The analysis results of the 13 proteins showing statistically-significant differences are more specifically shown in Table 9. In Table 9, the area under ROC curve (AUC) and the P value; the cutoff values expressed as concentration and probability score; and the sensitivities for different stages (Stage 0, Stage I, Stage II, Stage III, Stage IV) and all stages (All Stages) of colon

Reference Example 3

The effectiveness of a combined use of colon cancer markers for increasing the detection rate of colon cancer patients was verified.

The levels of almost all the 13 markers selected in Reference Example 2 in the plasma samples of the healthy individuals were relatively low. On the other hand, the plasma samples of the colon cancer patients had relatively high marker levels, and some of them had very high marker levels (i.e., outliers). A histogram representing the concentration (marker level) of Galectin-4 in the plasma samples of the healthy individuals and a histogram representing the concentration of Galectin-4 in the plasma samples of the colon cancer patients are shown in FIG. 1(a) by way of example. In FIG. 1(a), the horizontal axis represents the marker level of Galectin-4 and the vertical axis represents the number of samples. As shown in FIG. 1(a), the marker levels of the healthy individual group are well fitted with an extreme-value distribution function (represented by a curve in FIG. 1(a)). On the other hand, it was confirmed that some of the plasma samples of the cancer patient group had very high marker levels. For this reason, it can be considered that it is difficult to detect colon cancer patients simply by using linear classification.

In view of the above, the marker levels were sigmoidally normalized based on an extreme-value distribution. The parameters of the extreme-value distribution were determined using only the marker levels of the samples of the healthy individuals, and the marker level of each of the samples was converted to a "probability score" (hereinafter, sometimes simply referred to as a "score") by the cumulative distribution function of the extreme-value distribution. The thus obtained curve of probability score is shown in FIG. 1(b). In FIG. 1(b), the horizontal axis represents the marker level (raw value) of Galectin-4 and the vertical axis represents the probability score. The probability score refers to the probability that a patient has colon cancer at a certain marker level, and is a normalized value between 0 and 1. Therefore, a higher marker level that is less likely to be detected in the healthy individual group brings the probability score closer to 1.

After each of the marker levels was normalized in the same manner as described above, the average of normalized scores was used as an index to discriminate between colon cancer patients and healthy individuals. Combinations of markers effective in discriminating between colon cancer patients and healthy individuals were determined in the following manner using a Monte-Carlo method.

For example, in the case of analysis of a combination of two markers, the step of estimating parameters for normalization using 50 samples selected from the 100 samples of the healthy individuals and performing discrimination between colon cancer patients and healthy individuals using the remaining 50 samples of the healthy individuals and 53 samples selected from the 105 samples of the colon cancer patients was repeated 100 times (100-times analysis). In this way, the averages of scores at the time when two markers randomly selected from the 40 markers shown in Tables 1 to 8 were used in combination were calculated.

Further, in the case of analysis of a combination of three markers, the step of estimating parameters for normalization using 50 samples selected from the 100 samples of the healthy individuals and performing discrimination between colon cancer patients and healthy individuals using the remaining 50 samples of the healthy individuals and 53 samples selected from the 105 samples of the colon cancer patients was repeated 100 times (100-times analysis). In this way, the averages of scores at the time when three markers randomly selected from the 40 markers shown in Tables 1 to 8 were used in combination were calculated.

The above-described 100-times analysis was performed in the same manner as described above on combinations of 4, 5, 6, . . . and 40 markers, and the averages of scores were calculated.

Figure 2:
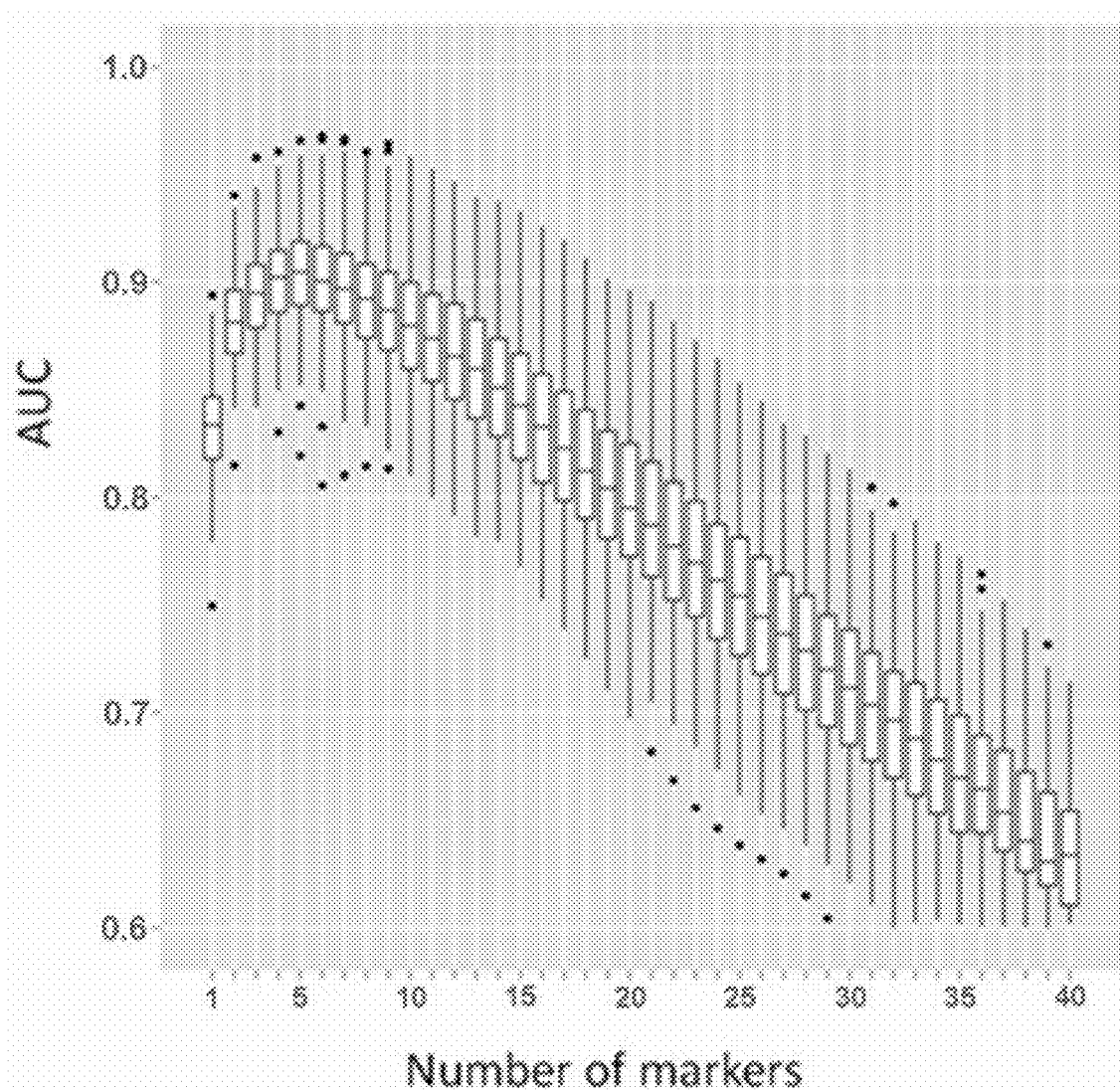
FIG. 2 is a graph showing the results of evaluation of the number of markers used in combination, wherein the horizontal axis represents the number of markers used in combination (Number of markers) and the vertical axis represents the area under ROC curve (AUC).

The obtained results were reevaluated based on a receiver operating characteristic (ROC) curve. The relationship between the number of markers used in combination (Number of markers) and the average of the areas under the ROC curve (AUC) is shown by a box plot in FIG. 2. In FIG. 2, the result of a case where a single marker was selected is also shown. In the box plot, each box represents a range where the dispersion in AUC averages of the results of 100 times of analyses is within 75%.

FIG. 2 shows the result that a combination of 5 markers is expected to be most efficient for detecting cancer.

Figure 3:
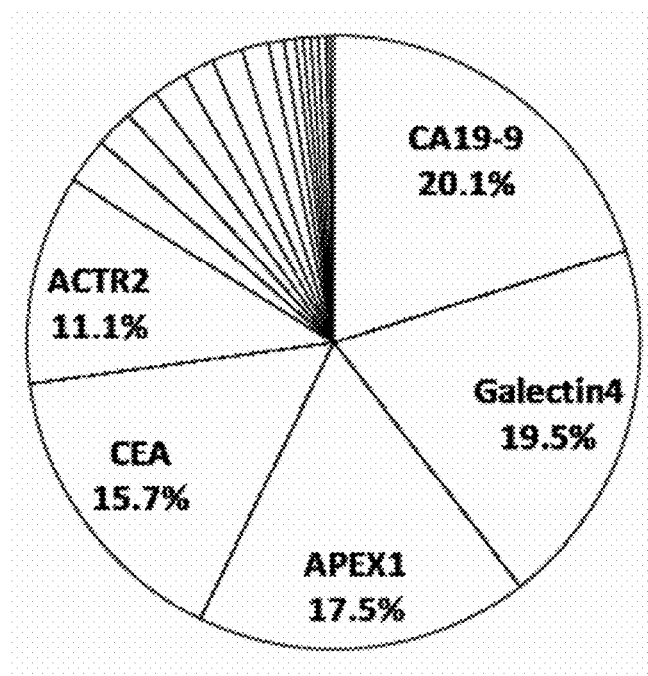
FIG. 3 is a circle graph showing the selection frequencies of individual markers in 100-times analysis performed using five markers in combination in Reference Example 3.
Figure 4:
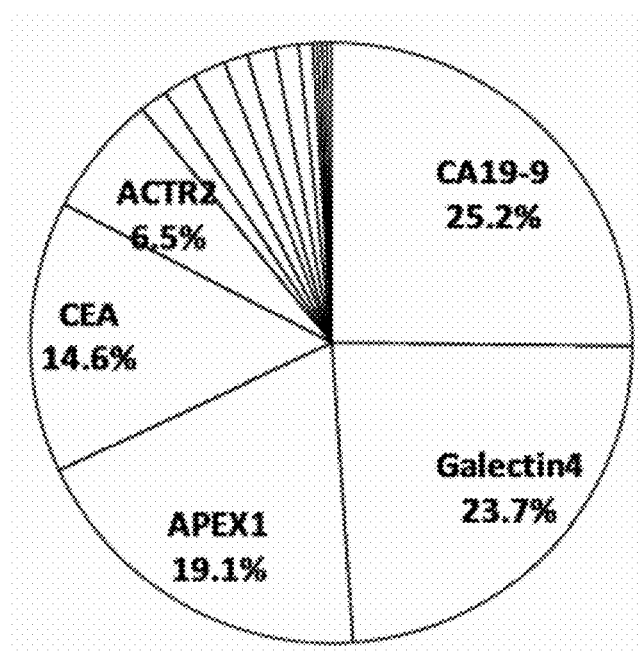
FIG. 4 is a circle graph showing the selection frequencies of individual markers in 100-times analysis performed using four markers in combination in Reference Example 3.
Figure 5:
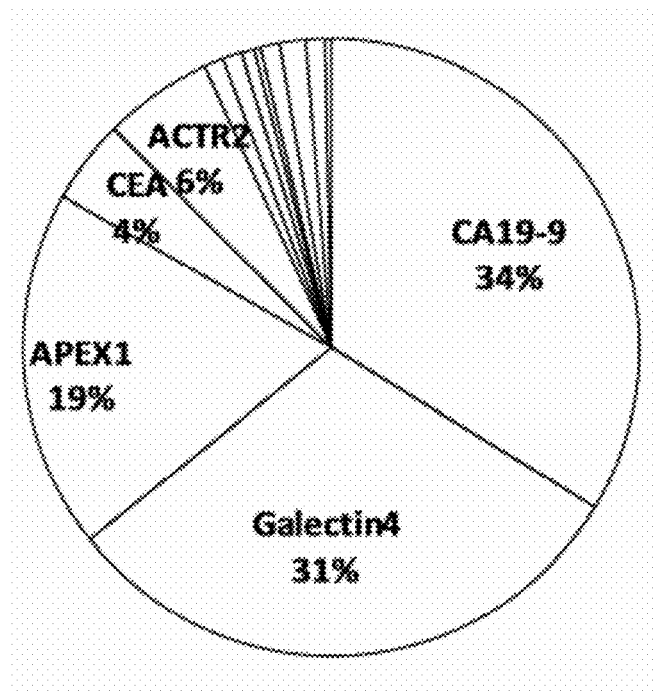
FIG. 5 is a circle graph showing the selection frequencies of individual markers in 100-times analysis performed using three markers in combination in Reference Example 3.
Figure 6:
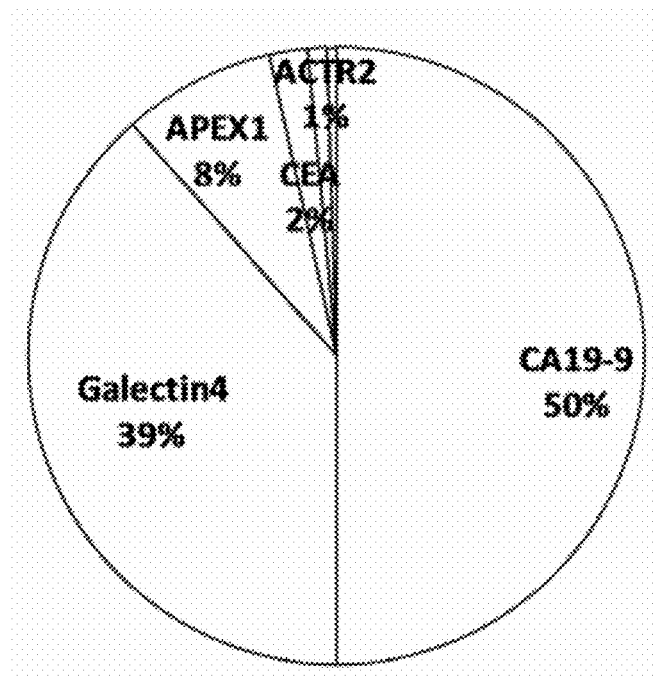
FIG. 6 is a circle graph showing the selection frequencies of individual markers in 100-times analysis performed using two markers in combination in Reference Example 3.

FIG. 3 is a graph showing the selection frequencies of individual markers in the above-described 100-times analysis using 5 markers. Similarly, FIG. 4 is a graph showing the selection frequencies of individual markers in the above-described 100-times analysis using 4 markers, FIG. 5 is a graph showing the selection frequencies of individual markers in the above-described 100-times analysis using 3 markers, and FIG. 6 is a graph showing the selection frequencies of individual markers in the above-described 100-times analysis using 2 markers. In all these cases, top five markers were Carbohydrate antigen 19-9 (CA19-9), Galectin-4, APEX nuclease (APEX1), Carcinoembryonic antigen-related cell adhesion molecule 5 (CEA), and Actin-related protein 2 (ACTR2).

Example 1

Combinations of two to five of the above-described top five markers frequently selected in Reference Example 3 (CA19-9, Galectin-4, APEX1, CEA, and ACTR2) were used in cancer marker panels to determine the ability of each of the cancer marker panels to detect colon cancer. The results are shown in Table 10. In Table 10, the area of under the ROC curve (AUC); the cutoff value represented as probability score; and the sensitivities for different stages (Stage 0, Stage I, Stage II, Stage III, and Stage IV) and all stages (All Stages) of colon cancer determined using the cutoff value of each of the combinations in healthy individuals vs colon cancer patients (Control vs CRC) are shown. It is to be noted that the cutoff value and the sensitivities are values when the specificity is 95% (i.e., when an allowable false-positive rate is 5%). Further, the cancer marker panels according to the present invention are marked with an asterisk.

TABLE 10

| | Combination | Control vs CRC AUC (Area under the ROC Curve) | Cutoff Value | Sensitivity | | | | | |
|---|---|---|---|---|---|---|---|---|---|
| | | | | Stage 0 (N = 6) | Stage I (N = 28) | Stage II (N = 25) | Stage III (N = 27) | Stage IV (N = 19) | All Stages |
| 2 marker | CEA_CA19-9 | 0.836 | 0.884 | 0.333 | 0.179 | 0.520 | 0.481 | 0.579 | 0.419 |
| | CEA_Galectin4 | 0.795 | 0.830 | 0.167 | 0.286 | 0.560 | 0.481 | 0.842 | 0.495 |
| | CEA_APEX1 | 0.784 | 0.839 | 0.167 | 0.036 | 0.480 | 0.296 | 0.632 | 0.324 |

TABLE 10-continued

| | Combination | Control vs CRC AUC (Area under the ROC Curve) | Cutoff Value | Sensitivity | | | | | |
|---|---|---|---|---|---|---|---|---|---|
| | | | | Stage 0 (N = 6) | Stage I (N = 28) | Stage II (N = 25) | Stage III (N = 27) | Stage IV (N = 19) | All Stages |
| | CEA_ACTR2 | 0.768 | 0.690 | 0.167 | 0.107 | 0.360 | 0.296 | 0.421 | 0.276 |
| | *CA19-9_Galectin4 | 0.887 | 0.874 | 0.500 | 0.321 | 0.400 | 0.519 | 0.526 | 0.438 |
| | *CA19-9_APEX1 | 0.850 | 0.914 | 0.167 | 0.107 | 0.400 | 0.407 | 0.368 | 0.305 |
| | CA19-9_ACTR2 | 0.826 | 0.786 | 0.167 | 0.107 | 0.360 | 0.333 | 0.211 | 0.248 |
| | Galectin4_APEX1 | 0.813 | 0.862 | 0.333 | 0.179 | 0.440 | 0.296 | 0.526 | 0.343 |
| | Galectin4_ACTR2 | 0.800 | 0.802 | 0.167 | 0.000 | 0.240 | 0.185 | 0.211 | 0.152 |
| | APEX1_ACTR2 | 0.772 | 0.768 | 0.167 | 0.036 | 0.240 | 0.111 | 0.158 | 0.133 |
| 3 marker | *CEA_CA19-9_Galectin4 | 0.876 | 0.800 | 0.333 | 0.393 | 0.760 | 0.556 | 0.789 | 0.590 |
| | *CEA_CA19-9_APEX1 | 0.862 | 0.794 | 0.333 | 0.286 | 0.600 | 0.593 | 0.579 | 0.495 |
| | *CEA_CA19-9_ACTR2 | 0.855 | 0.637 | 0.333 | 0.250 | 0.640 | 0.630 | 0.684 | 0.524 |
| | *CEA_Galectin4_APEX1 | 0.839 | 0.790 | 0.333 | 0.143 | 0.640 | 0.481 | 0.684 | 0.457 |
| | CEA_Galectin4_ACTR2 | 0.827 | 0.714 | 0.167 | 0.000 | 0.480 | 0.333 | 0.474 | 0.295 |
| | CEA_APEX1_ACTR2 | 0.812 | 0.670 | 0.167 | 0.071 | 0.440 | 0.407 | 0.421 | 0.314 |
| | *CA19-9_Galectin4_APEX1 | 0.892 | 0.783 | 0.500 | 0.321 | 0.760 | 0.630 | 0.632 | 0.571 |
| | *CA19-9_Galectin4_ACTR2 | 0.883 | 0.679 | 0.333 | 0.250 | 0.640 | 0.593 | 0.526 | 0.486 |
| | *CA19-9_APEX1_ACTR2 | 0.860 | 0.652 | 0.500 | 0.179 | 0.640 | 0.519 | 0.526 | 0.457 |
| | Galectin4_APEX1_ACTR2 | 0.829 | 0.743 | 0.333 | 0.000 | 0.400 | 0.185 | 0.368 | 0.229 |
| 4 marker | *CEA_CA19-9_Galectin4_APEX1 | 0.895 | 0.753 | 0.333 | 0.321 | 0.720 | 0.593 | 0.737 | 0.562 |
| | *CEA_CA19-9_Galectin4_ACTR2 | 0.892 | 0.655 | 0.500 | 0.357 | 0.720 | 0.704 | 0.737 | 0.610 |
| | *CEA_CA19-9_APEX1_ACTR2 | 0.880 | 0.636 | 0.667 | 0.286 | 0.680 | 0.667 | 0.526 | 0.543 |
| | *CEA_Galectin4_APEX1_ACTR2 | 0.856 | 0.686 | 0.167 | 0.071 | 0.600 | 0.519 | 0.632 | 0.419 |
| | *CA19-9_Galectin4_APEX1_ACTR2 | 0.894 | 0.696 | 0.333 | 0.179 | 0.640 | 0.704 | 0.526 | 0.495 |
| 5 marker | *CEA_CA19-9_Galectin4_APEX1_ACTR2 | 0.907 | 0.630 | 0.500 | 0.357 | 0.800 | 0.778 | 0.737 | 0.648 |

In Example 1, samples whose average of probability scores of the markers exceeded the cutoff value shown in Table 10 were regarded as positive to discriminate between healthy individuals and colon cancer patients.

The AUC value was highest when the 5 markers (CA19-9, CEA, Galectin-4, APEX1, and ACTR2) were used in combination, and it has been confirmed that the combination of the 5 markers has the highest ability to discriminate between cancer patients and healthy individuals. Further, it has been also confirmed that all the other combinations of markers according to the present invention marked with an asterisk have a higher AUC value than the combination of conventional markers CEA and CA19-9.

Further, when sensitivity was compared, sensitivity was most improved particularly when the above-mentioned 5 markers were used in combination.

Figure 7:
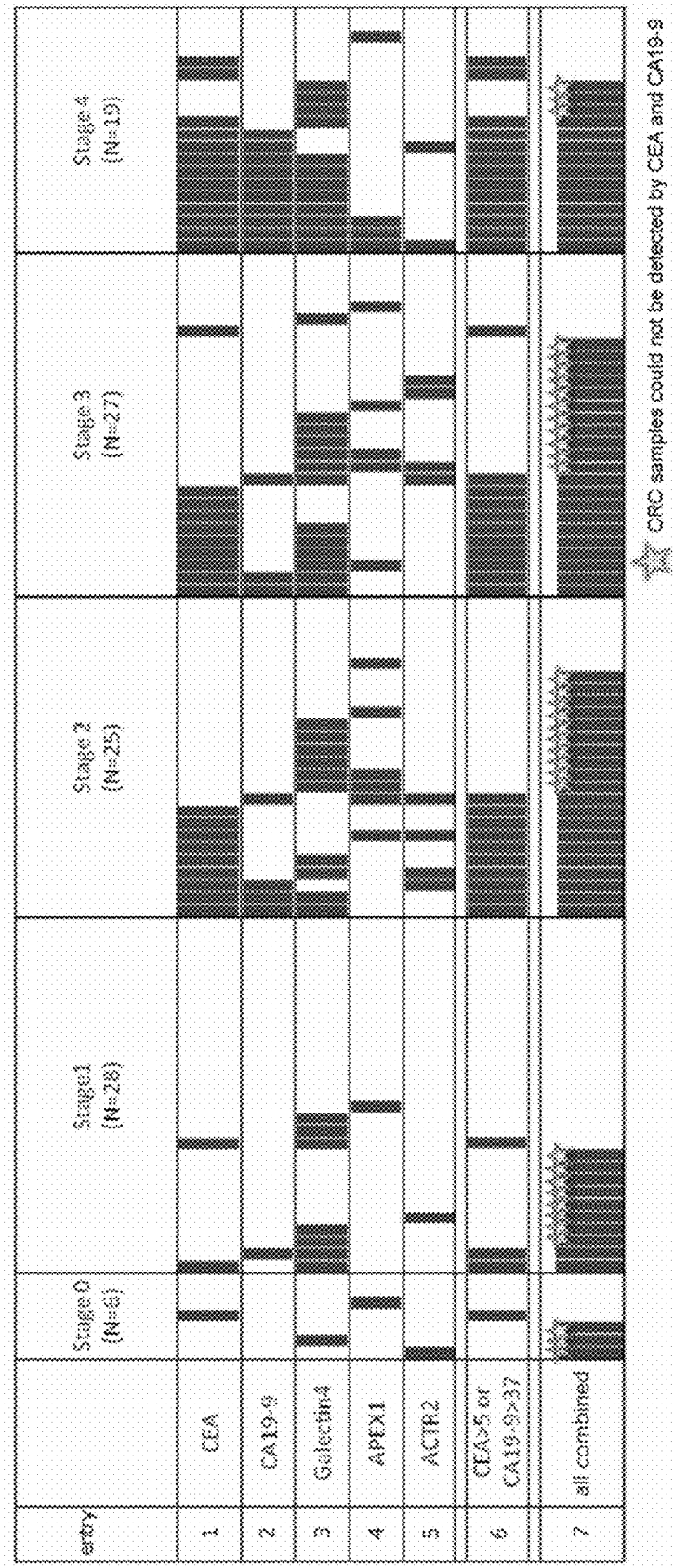
FIG. 7 shows samples diagnosed as cancer when five markers constituting a cancer marker panel according to the present invention were used singly and samples diagnosed as cancer when all the five markers were used in combination.

Further, a comparison was made using the positive plasma samples between when the each of the above-mentioned 5 markers was used alone and when the above-mentioned 5 markers were used in combination. The results are shown in FIG. 7. In FIG. 7, in Entries 1 to 5 (for comparison), samples regarded as positive when each of the markers was used alone are represented by filled bars, in Entry 6 (for comparison), samples regarded as positive when at least one of CEA and CA19-9 (CEA>5 ng/mL and/or CA19-9>37 U/mL) was used are represented by filled bars, and in Entry 7 (all combined), samples regarded as positive when all the 5 markers were used in combination are represented by filled bars. A symbol "star" on the bars indicates that the CRC samples could not be detected by CEA and CA19-9. It is to be noted that in Entry 7, samples whose average of probability scores of the markers exceeded the cutoff value were regarded as positive.

As can be seen from FIG. 7, sensitivity in patients with early stage (Stage 0 and Stage I) cancer is particularly significantly improved when all the 5 markers are used in combination as compared to when at least one of CEA and CA19-9 is used. From the result, it has been found that the use of Galectin-4, APEX1, and ACTR2 makes it possible to complementarily detect samples in the relatively early stages of cancer that cannot be detected by established colon cancer markers CEA and CA19-9.

What is claimed is:

1. A method of detecting colon cancer markers in a subject, comprising
   measuring, by an assay based on biospecific affinity or a quantitative mass spectrometry method, colon cancer markers in a blood plasma sample from the subject, wherein the colon cancer markers measured by the method consist of Carcinoembryonic antigen-related cell adhesion molecule 5, Carbohydrate antigen 19-9, Galectin-4, APEX nuclease, and Actin-related protein 2.

2. The method according to claim 1, wherein the subject is human.

3. The method according to claim 1, wherein the measuring comprises the biospecific affinity method.

4. The method according to claim 3, wherein the biospecific affinity method is immunoassay.

5. The method according to claim 4, wherein the immunoassay comprises at least one selected from the group consisting of western blotting, radioimmunoassay, Enzyme-Linked ImmunoSorbent Assay, immunoprecipitation, precipitation reaction, immunodiffusion, immunoagglutination, complement-binding reaction, immunoradiometric assay, fluoroimmunoassay, and protein A immunoassay.

6. The method according to claim 4, wherein the immunoassay comprises ELISA measurement.

7. The method according to claim 1, wherein the measuring comprises the quantitative mass spectrometry method.

8. The method according to claim 1, wherein the subject is diagnosed with colon cancer.

9. The method according to claim 1, wherein the subject is not diagnosed with colon cancer.

10. The method according to claim 1, further comprising obtaining a blood sample from a patient and treating the blood sample to obtain the blood plasma sample.

11. A method of detecting colon cancer markers in a subject, comprising
   detecting colon cancer markers in a blood plasma sample from the subject, wherein the colon cancer markers detected by the method consist of Carcinoembryonic antigen-related cell adhesion molecule 5, Carbohydrate antigen 19-9, Galectin-4, APEX nuclease, and Actin-related protein 2.

12. The method according to claim 11, wherein the subject is human.

13. The method according to claim 11, wherein the detecting comprises the biospecific affinity method.

14. The method according to claim 13, wherein the biospecific affinity method is immunoassay.

15. The method according to claim 14, wherein the immunoassay comprises at least one selected from the group consisting of western blotting, radioimmunoassay, Enzyme-Linked ImmunoSorbent Assay, immunoprecipitation, precipitation reaction, immunodiffusion, immunoagglutination, complement-binding reaction, immunoradiometric assay, fluoroimmunoassay, and protein A immunoassay.

16. The method according to claim 11, wherein the subject is diagnosed with colon cancer.

17. The method according to claim 11, wherein the subject is not diagnosed with colon cancer.

18. The method according to claim 11, further comprising obtaining a blood sample from a patient and treating the blood sample to obtain the blood plasma sample.

\* \* \* \* \*